United States Patent
Ju et al.

(10) Patent No.: US 6,217,566 B1
(45) Date of Patent: Apr. 17, 2001

(54) PERIPHERAL VASCULAR DELIVERY CATHETER

(75) Inventors: Byung H. Ju, Miyazaki (JP); Jose D. Alejandro, San Jose, CA (US)

(73) Assignee: Target Therapeutics, Inc., Fremont, CA (US)

( * ) Notice: Subject to any disclaimer, the term of this patent is extended or adjusted under 35 U.S.C. 154(b) by 0 days.

(21) Appl. No.: 08/943,036

(22) Filed: Oct. 2, 1997

(51) Int. Cl.⁷ .................................. A61M 25/00
(52) U.S. Cl. ............................... 604/526; 604/527
(58) Field of Search .................... 604/264, 265, 604/280, 282, 525, 526, 527; 600/433–435; 138/155

(56) References Cited

U.S. PATENT DOCUMENTS

| | | |
|---|---|---|
| 243,396 | 6/1881 | Pfarre . |
| 2,211,975 | 8/1940 | Hendrickson . |
| 2,437,542 | 3/1948 | Krippendorf . |
| 3,174,851 | 3/1965 | Buehler et al. . |
| 3,351,463 | 11/1967 | Rozner et al. . |
| 3,416,531 | 12/1968 | Edwards . |
| 3,753,700 | 8/1973 | Harrison et al. . |
| 3,757,768 | 9/1973 | Kline . |
| 3,924,632 | 12/1975 | Cook . |
| 4,425,919 | 1/1984 | Alston, Jr. et al. . |
| 4,430,083 | 2/1984 | Ganz et al. . |
| 4,484,586 | 11/1984 | McMickle et al. . |
| 4,516,972 | 5/1985 | Samson . |
| 4,657,024 | 4/1987 | Coneys . |
| 4,676,229 | 6/1987 | Krasnicki et al. . |
| 4,737,153 | 4/1988 | Shimamura et al. . |
| 4,806,182 | 2/1989 | Rydell et al. . |
| 4,832,681 | 5/1989 | Lenck . |
| 4,899,787 | 2/1990 | Ouchi et al. . |
| 4,981,478 | 1/1991 | Evard et al. . |
| 4,985,022 | 1/1991 | Fearnot et al. . |
| 5,037,404 | 8/1991 | Gold et al. . |
| 5,057,092 | 10/1991 | Webster, Jr. . |
| 5,069,674 | 12/1991 | Fearnot et al. . |
| 5,085,649 | * 2/1992 | Flynn . |
| 5,156,785 | 10/1992 | Zdrahala . |
| 5,176,660 | 1/1993 | Truckai . |
| 5,178,158 | 1/1993 | de Toledo . |
| 5,180,376 | 1/1993 | Fischell . |
| 5,184,627 | 2/1993 | de Toledo . |
| 5,217,482 | 6/1993 | Keith . |
| 5,222,949 | 6/1993 | Kaldany . |
| 5,248,305 | * 9/1993 | Zdrahala . |
| 5,312,356 | * 5/1994 | Engelson et al. . |
| 5,313,967 | 5/1994 | Lieber et al. . |

(List continued on next page.)

FOREIGN PATENT DOCUMENTS

| | | |
|---|---|---|
| 0098100 | 1/1984 | (EP) . |
| 0421650-A1 | 4/1991 | (EP) . |
| WO 92/07507 | 5/1992 | (WO) . |
| WO 93/05842 | 4/1993 | (WO) . |
| WO 93/15785 | 8/1993 | (WO) . |
| WO 95/28982 | 11/1995 | (WO) . |
| WO 96/33763 | 10/1996 | (WO) . |

*Primary Examiner*—Anhtuan T. Nguyen
(74) *Attorney, Agent, or Firm*—Morrison & Foerster LLP (57) ABSTRACT

This is a delivery catheter assembly used typically, but not exclusively, in the peripheral vasculature of the human body. The catheter is configured in such a way that the lumen is exceptionally large and the catheter wall is exceptionally thin for a catheter of this class. The distal portion of the catheter contains a kink-resisting member, preferably a super-elastic alloy ribbon braid, which is embedded in the catheter wall. Proximally of the kink-resisting member, the catheter typically will have no other kink-resisting members. Finally, the catheter assembly uses long conical joints between component tubular members to provide smooth and strong transitions between those members.

29 Claims, 4 Drawing Sheets

U.S. PATENT DOCUMENTS

| | | |
|---|---|---|
| 5,318,032 * | 6/1994 | Lonsbury et al. . |
| 5,405,338 | 4/1995 | Kranys . |
| 5,454,795 | 10/1995 | Samson . |
| 5,496,294 * | 3/1996 | Hergenrother et al. . |
| 5,531,715 | 7/1996 | Engelson et al. . |
| 5,531,721 * | 7/1996 | Pepin et al. . |
| 5,533,985 * | 7/1996 | Wang . |
| 5,538,512 | 7/1996 | Zenzon et al. . |
| 5,571,073 * | 11/1996 | Castillo . |
| 5,584,821 * | 12/1996 | Hobbs et al. . |
| 5,599,325 * | 2/1997 | Ju et al. . |
| 5,702,373 * | 12/1997 | Samson . |
| 5,769,830 * | 6/1998 | Parker . |

* cited by examiner

PERIPHERAL VASCULAR DELIVERY CATHETER

FIELD OF THE INVENTION

This invention is a surgical device. In particular, it is a delivery catheter assembly used typically, but not exclusively, in the peripheral vasculature of the human body. The catheter is configured in such a way that the lumen is exceptionally large and the catheter wall is exceptionally thin for a catheter of this class. The distal portion of the catheter contains a kink-resisting member, preferably a super-elastic alloy ribbon braid, which is embedded in the catheter wall. Proximally of the kink-resisting member, the catheter typically will have no other kink-resisting members. Finally, the catheter assembly uses long conical joints between component tubular members to provide smooth and strong transitions between those members.

BACKGROUND OF THE INVENTION

Catheters are increasingly used to access remote regions of the human body, and in doing so, delivering diagnostic or therapeutic agents to those sites. In particular, catheters which use the circulatory system as the pathway to these treatment sites have become especially practical over the past ten years.

Often the site which one desires to access by catheter is within a soft tissue such as the liver. Although the liver itself is relatively easy to reach, it is not straightforward to progress deep into the liver. A catheter must be passed through ever-narrower regions of the arterial system until the catheter reaches a selected site. It is apparent that to reach sites deep within an organ such as the liver, the outside diameter of a catheter should be small. However, it is often the case that merely reducing the outside diameter of a catheter will significantly increase a catheter's propensity for kinking and does not improve its ability to follow guidewires of sophisticated design, into distant reaches of the vasculature. To provide sufficient pushability, kink-resistance, and fluid flow capabilities is not a trivial task. As to the latter requirement, it should be apparent that delivery of fluid through a small lumen catheter can be difficult and even dangerous if the lumen is too small. High pressures produced even by the smallest of syringes can rupture a small lumen catheter or even detach a distal tip if the wall of the catheter is too weak to withstand such flowing pressures.

The delivery catheter of this invention uses two features, among others, to provide a delivery catheter having a very large lumen for the class of catheters described, high kink-resistance, and a substantial burst resistance.

The kink-resisting member is preferably a woven braid produced from a number of super-elastic alloy ribbons. The kink-resisting alloy is embedded in a thermoplastic layer. The catheter is preferably built without butt joints in the assembly because of the inability of these joints to withstand high pressure. The catheter in this invention utilizes very shallow conical joints to provide a significant surface area between adjoining tubular members so to provide both superior strength and smooth transitions in flexibility and material from one section to another. We have found that by optimization of these joints, the wall of the catheter may be made significantly thinner than in other devices of the same class and consequently the lumen may be made significantly larger as well. For instance, a typical catheter made using the two tenets of the invention described above may be made in a 2.7 French size and yet have a larger lumen in commercial 3 French catheters made using conventional techniques.

Devices such as these are used to provide fluid materials such as dyes and treatment materials to sites in the body. These fluids are often viscous and difficult to inject. Furthermore, these catheters are used to occlude blood flow to portions of the treated organ. Since it is desirable to treat the smallest possible effective region of the organ, small diameter catheters with larger diameter lumen are highly desirable.

There are other ways of causing a catheter to proceed through the human vasculature to a selected site, but a guidewire-aided catheter is considered to be both quite quick and somewhat more accurate than the other procedures. One such alternative procedure is the use of a flow-directed catheter. These devices often have a small balloon situated on the distal end of the catheter which may be alternately deflated and inflated as the need to select a route for the catheter is encountered.

This invention is an adaptable one and may be used in a variety of catheter formats. The invention utilizes the concept of combining one or more polymeric tubes with a metallic braid comprising ribbons of a super-elastic alloy. The construction technique has the benefit of producing catheter sections having small overall diameters but with exceptional strength, resistance to kinking, and recovery from kinking (even in vivo) should such kinking occur.

The use of braids in a catheter body is not a novel concept. Typical background patents are discussed below. However, none of these documents have used our concept to produce a catheter which has the physical capabilities of the catheter of this invention.

Multi-Wrap Catheters

There are a number of catheters discussed in the literature which utilize catheter bodies having multiply-wrapped reinforcing material. These catheters include structures having braided bands or ones in which the spirally wound material is simply wound in one direction and the following layer or layers are wound in the other.

Krippendorf, U.S. Pat. No. 2,437,542, describes a "catheter-type instrument" which is typically used as a ureteral or urethral catheter. The physical design is said to be one having a distal section of greater flexibility and a proximal section of lesser flexibility. The device is made of intertwined threads of silk, cotton, or some synthetic fiber. It is made by impregnating a fabric-based tube with a stiffening medium which renders the tube stiff yet flexible. The thus-plasticized tubing is then dipped in some other medium to allow the formation of a flexible varnish-like layer. This latter material may be a tung oil base or a phenolic resin and a suitable plasticizer. There is no indication that this device is of the flexibility described herein. Additionally, it appears to be the type which is used in some region other than in the body's periphery or in its soft tissues.

Similarly, U.S. Pat. No. 3,416,531, to Edwards, shows a catheter having braiding-edge walls. The device further has additional layers of other polymers such as TEFLON and the like. The strands found in the braiding in the walls appear to be threads having circular cross-sections. There is no suggestion of constructing a device using ribbon materials. Furthermore, the device is shown to be fairly stiff in that it is designed so that it may be bent using a fairly large handle at its proximal end.

U.S. Pat. No. 3,924,632, to Cook, shows a catheter body utilizing fiberglass bands wrapped spirally for the length of the catheter. As is shown in FIG. 2 and the explanation of the Figure at column 3, lines 12 and following, the catheter uses fiberglass bands which are braided, that is to say, bands which are spiraled in one direction cross over and under bands which are spiraled in the opposite direction. Additionally, it should be observed that FIG. 3 depicts a catheter shaft having both an inner lining or core 30 and an outer tube 35.

U.S. Pat. No. 4,425,919, to Alston, Jr. et al., shows a multilayered catheter assembly using multi-stranded flat wire braid. The braid 14 in FIG. 3 further covers an interior tubing or substrate 12.

U.S. Pat. No. 4,484,586 shows a method for the production of a hollow, conductive medical tubing. The conductive wires are placed in the walls of hollow tubing specifically for implantation in the human body, particularly for pacemaker leads. The tubing is preferably made of an annealed copper wire which has been coated with a body-compatible polymer such as a polyurethane or a silicone. After coating, the copper wire is wound into a tube. The wound substrate is then coated with still another polymer to produce a tubing having spiral conducting wires in its wall.

A document showing the use of a helically wound ribbon of flexible material in a catheter is U.S. Pat. No. 4,516,972, to Samson. This device is a guiding catheter and it may be produced from one or more wound ribbons. The preferred ribbon is a polyaramid material known as Kevlar 49. Again, this device is a device which must be fairly stiff. It is a device which is designed to take a "set" and remain in a particular configuration as another catheter is passed through it. It must be soft enough so as not to cause substantial trauma, but it is certainly not for use with a guidewire. It would not meet the flexibility criteria required of the inventive catheter described herein.

U.S. Pat. No. 4,806,182, to Rydell et al, shows a device using a stainless steel braid imbedded in its wall and having an inner layer of a polyfluorocarbon. The process also described therein is a way to laminate the polyfluorocarbon to a polyurethane inner layer so as to prevent delamination.

U.S. Pat. No. 4,832,681, to Lenck, shows a method and apparatus useful for artificial fertilization. The device itself is a long portion of tubing which, depending upon its specific materials of construction, may be made somewhat stiffer by the addition of a spiral reinforcement comprising stainless steel wire.

U.S. Pat. No. 4,981,478, to Evard et al., discloses a multi-sectioned or composite vascular catheter. The interior section of the catheter appears to have three sections making up the shaft. The most interior (and distal) section, 47, appears to be a pair of coils 13 and 24 having a polymeric tubing member 21 placed within it. The next, more proximal, section is 41, and FIG. 4 shows it to be "wrapped or braided" about the next inner layer discussed just above. The drawing does not show it to be braided but, instead, a series of spirally wrapped individual strands. Finally, the outermost tubular section of this catheter core is another fiber layer 49, of similar construction to the middle section 26 discussed just above.

Another catheter showing the use of braided wire is shown in U.S. Pat. No. 5,037,404, to Gold et al. Mention is made in Gold et al of the concept of varying the pitch angle between wound strands so to result in a device having differing flexibilities at differing portions of the device. The differing flexibilities are caused by the difference in pitch angle. No mention is made of the use of ribbon, nor is any specific mention made of the particular uses to which the Gold et al. device may be placed.

U.S. Pat. No. 5,057,092, to Webster, Jr., shows a catheter device used to monitor cardiovascular electrical activity or to electrically stimulate the heart. The catheter uses braided helical members having a high modulus of elasticity, e.g., stainless steel. The braid is a fairly complicated, multi-component pattern shown very well in FIG. 2.

U.S. Pat. No. 5,176,660 shows the production of catheters having reinforcing strands in their sheath wall. The metallic strands are wound throughout the tubular sheath in a helical crossing pattern so to produce a substantially stronger sheath. The reinforcing filaments are used to increase the longitudinal stiffness of the catheter for good "pushability". The device appears to be quite strong and is wound at a tension of about 250,000 lb./in.$^2$ or more. The flat strands themselves are said to have a width of between 0.006 and 0.020 inches and a thickness of 0.0015 and 0.004 inches. There is no suggestion to use these concepts in devices having the flexibility and other configurations described below.

Another variation which utilizes a catheter wall having helically placed liquid crystal fibrils is found in U.S. Pat. No. 5,248,305, to Zdrahala. The catheter body is extruded through an annular die, having relatively rotating inner and outer mandrel dies. In this way, the tube containing the liquid crystal polymer (LCP) plastic-containing material exhibits a bit of circumferential orientation due to the rotating die parts. At column 2, line 40 and following, the patent suggests that the rotation rate of the inner and outer walls of the die may be varied as the tube is extruded, with the result that various sections of the extruded tube exhibit differing stiffnesses.

U.S. Pat. No. 5,217,482 shows a balloon catheter having a stainless steel hypotube catheter shaft and a distal balloon. Certain sections of the device shown in the patent use a spiral ribbon of stainless steel secured to the outer sleeve by a suitable adhesive to act as a transition section from a section of very high stiffness to a section of comparatively low stiffness.

Japanese Kokai 05-220,225, owned by the Terumo Corporation, describes a catheter in which the torsional rigidity of the main body is varied by incorporating onto an inner tubular section 33, a wire layer which is tightly knitted at the proximal section of the catheter and more loosely knitted at a midsection.

Single-Layer, Reinforced Catheters

There are a variety of catheters which, unlike the devices discussed above, utilize but a single layer of reinforcing material.

For instance, U.S. Pat. No. 243,396 to Pfarre, patented in June of 1881, shows the use of a surgical tube having a wire helix situated within the tube wall. The wire helix is said to be vulcanized into the cover of the device.

U.S. Pat. No. 2,211,975, to Hendrickson, shows a similar device also comprising a stainless steel wire 15 embedded in the inner wall of a rubber catheter.

U.S. Pat. No. 3,757,768, to Kline, shows a "unitary, combined spring guide-catheter that includes an inner wall portion formed as a continuous helical spring with the helices in contact with each other and an outer wall portion formed from an inert plastic material enclosing the spring in such a manner as to become firmly bonded to the spring while having its outer surface smooth". There is no suggestion to separate the windings of the coil in any fashion.

U.S. Pat. No. 4,430,083 describes a catheter used for percutaneous administration of a thrombolytic agent directly to a clot in a coronary artery. The device itself is an elongated, flexible tube supported by helically wound wire having a specific cross-sectional shape. The wire is wound into a series of tight, contiguous coils to allow heat shrinking of tubing onto the outside of the wire of the shape of the outer surface of the wire as wound into the helix provides the heat-shrunk tubing with footing for a tight fit.

U.S. Pat. No. 4,657,024, to Coneys, shows a catheter which employs a set of helical strips within the wall of the catheter. However, the helical strips are of a radio-opaque material, e.g., fluorinated ethylene-propylene. It is not clear that the blended radio-opaque material necessarily provides any physical benefit other than the ability to allow the catheter shaft to be seen when viewed with a fluoroscope.

U.S. Pat. No. 4,737,153, to Shimamura et al., describes a device which is characterized as a "reinforced therapeutic tube" and which uses a spiral reinforcing material embedded within the wall of the device.

U.S. Pat. No. 5,069,674, to Fearnot et al. (and its parent, U.S. Pat. No. 4,985,022), shows a small diameter epidural catheter having a distal tip made up of a stainless steel wire which is helically wound and placed within a tubular sheath or tube. There is no suggestion within the patent that the interior coil be made to adhere to the outer tubular sheath.

Similarly, U.S. Pat. No. 5,178,158, to de Toledo, shows what is characterized as a "convertible wire for use as a guidewire or catheter". The patent describes a structure which comprises an interior wire or spring section shown, in the drawings, to be of generally rectangular cross-section. Outer layers of the device include a polyamide sheath placed adjacent to the helical coil at the proximal end of the catheter (see column 4, lines 64 and following). The device also comprises an outer sheath 40 of Teflon that extends from the proximal end 12 to the distal end 14 of the device. The overlying sheath 40 may extend or overhang at the proximal or the distal end of the catheter. The distal tip portion 13 is said to be "flexible, soft, and floppy". The PCT Published Application corresponding to this patent is WO 92/07507.

U.S. Pat. No. 5,184,627 shows a guidewire suitable for infusion of medicaments to various sites along the guidewire. The guidewire is made up of a helically wound coil having a polyamide sheath enclosing its proximal portion and a Teflon sheath tightly covering the entire wire coil. The coil is closed at its distal end. There is no suggestion that the wire forming the helical core be adhesively attached to its outer coverings.

U.S. Pat. No. 5,313,967, to Lieber et al., shows a medical device, a portion of which is a helical coil which apparently may include an outer plastic sheath in some variations. Apparently, a secondary helix of a somewhat similar design (in that it is formed by rotating a flat wire or the like along its longitudinal axis to form a screw-like configuration) is included within the helical coil to provide axial pushability and torque transmission.

U.S. Pat. No. 5,405,338, to Kranys, describes a helically wound catheter incorporating a shaft component having a helically wound coil with a skin or webbing supported by the coil. The skin or webbing is said to contribute "negligibly to the resistance of the catheter to axially directed compressive forces . . . " The catheter may include an inner, taut skin component.

The PCT application, WO 93/15785, to Sutton et al., describes kink-resistant tubing made up of a thin layer of an encapsulating material and a reinforcing coil. As is shown in the drawings, the supporting material is embedded within the wall of the tubing in each instance.

The PCT application bearing the number WO 93/05842, to Shin et al., shows a ribbon-wrapped catheter. The device is shown as a section of a dilatation catheter. The inner section 34 is a helically wound coil and is preferably a flat wire. See, page 6, lines 25 and following. The coil is then wrapped with a heat-shrunk jacket 34 formed of low-density polyethylene. A lubricious material such as a silicone coating may then be placed on the inner surface of the spring coil to "enhance handling of the guidewire". It is also said, on page 6 of the document, that the "entire spring coil, before it is wound or jacketed, may be coated with other materials such as Teflon to enhance lubricity or provide other advantages. In some embodiments, the spring coil has been plated with gold."

Endoscope Structures

Various endoscopic structures, used primarily in sizes which are larger than endovascular catheters utilize structures including stiffener materials.

U.S. Pat. No. 4,676,229, to Krasnicki et al., describes an endoscopic structure 30 having an ultra-thin walled tubular substrate 31 formed of a lubricious material such as TEFLON. The structure contains a filament supported substrate. The filament is coated with and embedded into a filler material, typically an elastomeric material. A highly lubricious outer coating 35, all as shown in FIG. 2, forms the outer layer of the device. FIG. 3 in Krasnicki et al., describes another variation of the endoscopic device in which a different selection of polymer tubing is utilized but the placement of the filamentary support remains varied in an intermediate material of an elastomer. In some variations of the device, the filament is strongly bonded to the inner tubular substrate using an adhesive 37 "such as an epoxy cement having sufficient bond strength to hold the filament to the substrate as it is deformed into a tight radius." See, column 3, lines 50 and following.

U.S. Pat. No. 4,899,787, to Ouchi et al. (and its foreign relative, German Offenlegungshrifft DE-3242449) describes a flexible tube for use in an endoscope having a flexible, basic tubular core structure made up of three parts. The three parts are an outer meshwork tube, an intermediate thermoplastic resin tube bonded to the outer meshwork tube, and an inner ribbon made of a stainless steel or the like which is adherent to the two polymeric and meshwork tubes such that the resin tube maintains an adherent compressive pressure in the finished flexible tube. The patent also suggests the production of an endoscope tube having "flexibility which varies in step-wise manner from one end of the tube to the other . . . [and is produced] by integrally bonding two or more thermoplastic resin tube sections formed of respective resin materials having different hardnesses to the outer surface of the tubular core structure . . . ". See, column 2, lines 48 and following.

U.S. Pat. No. 5,180,376 describes an introducer sheath utilizing a thin, flat wire metal coil surrounded only on its exterior surface with a plastic tube of coating. The flat wire coil is placed there to lower the "resistance of the sheath to buckling while minimizing the wall thickness of the sheath." A variation using two counter-wound metal ribbons is also described.

European Patent Application 0,098,100 describes a flexible tube for an endoscope which uses a helically wound metallic strip having a braided covering contiguous to the outer surface of the coil and having still further out a polymeric coating 9. Interior to the coil is a pair of slender flexible sheaths which are secured to a "front-end piece 10" by soldering.

Japanese Kokai 2-283,346, describes a flexible endoscope tube. The tubular outer shell is made up of two layers of a high molecular weight laminated material. The tube also has an inner layer of an elastic material and interior to it all is a metallic ribbon providing stiffening.

Japanese Kokai 03-023,830, also shows the skin for flexible tube used in an endoscope which is made up of a braid 3 prepared by knitting a fine wire of a metal with a flexible portion 2 which is prepared by spirally winding an elastic belt sheet-like material and a skin 4 with which the whole outer surface of the device is covered. The document appears to emphasize the use of a particular polyester elastomer.

Japanese Kokai 5-56,910, appears to show a multi-layered endoscope tube made up of layers of the spiral wound metallic ribbon covered by a polymeric sheath.

French Patent Document 2,613,231, describes a medical probe used with an endoscope or for some other device used to stimulate the heart. The device appears to be a helix having a spacing between 0 and 0.25 mm (See page 4, line 20) preferably rectangular in cross section (See Page 4, Line 1) and of a multi-phase alloy such as M35N, SYNTACOBEN, or ELGELOY (See Page 4).

German Offenlegungshrifft DE-3642107 describes an endoscope tube, formed of a spiral tube, a braid formed of fibers interwoven into a net (which braid is fitted on the outer peripheral surface of the spiral tube), and a sheath covering the outer peripheral surface of the braid.

None of the noted devices have the structure required by the claims recited herein.

Other Anti-kinking Configurations

U.S. Pat. No. 5,222,949, to Kaldany, describes a tube in which a number of circumferential bands are placed at regular intervals along a catheter shaft. The bands may be integrated into the wall of the catheter. A variety of methods for producing the bands in the tubular wall are discussed. These methods include periodically irradiating the wall to produce bands of a higher integral of cross-linking.

European Patent Application No. 0,421,650-A1 describes a method for producing a catheter from a roll of polymer film while incorporating other materials such as tinfoil elements or the like.

None of the documents cited above provides a structure required by the disclosure and claims recited below, particularly when the flexibility and ability to resist kinks is factored into the physical description of the devices.

SUMMARY OF THE INVENTION

This invention is a catheter assembly generally made up of three sections: a most-distal portion, a more proximal portion, and a junction region separating those two sections. The distal section utilizes a kink-resisting member, typically a woven braid of a super-elastic alloy. The more proximal section is most typically produced from a pair of polymeric layers without any kink-resisting members. The overall catheter assembly is produced without using butt joints in any of the fluid carrying tubular members.

Another central aspect to this invention is the use of very shallow conical surfaces in joining various polymeric tubular components. Proximal of the kink-resistant distal section is the junction region. The junction region may contain up to four or five layers of polymers, most of which taper in the region and are joined to other tubular components there. It is highly desirable that the length of the junction region, e.g., the length of the longest taper in the region, is as much as twelve times the diameter of the assembly at that region.

The kink-resisting member in the distal section may be a helically wound coil or a woven or unwoven braid. A woven braid is most desired, although any of these kink-resistant members may be employed in certain circumstances.

The catheter assembly most desirably has a polymeric, lubricious, tubular member forming the inside lumen. This lubricious member desirably extends from the distal end of the catheter and terminates there in a single opening and is continuous and unbroken through the catheter to the proximal end. A typical lubricious polymer for such a tubing would be polytetrafluoroethylene (PTFE). A variety of typical polymeric materials may be used for the remainder of the catheter, e.g., polyurethane, polyethylene, polyurethane-polycarbonate alloys and mixtures, polyvinylchloride, and the like. Mixtures of polyurethane and polycarbonate are preferred.

DESCRIPTION OF THE INVENTION

This invention includes a thin-walled, kink-resistant catheter assembly. It is typically used to access vascular sites within the human periphery vascular system. As will be described in more detail below, the device typically has a most distal section containing a kink-resistant member, desirably a woven braid of a super-elastic alloy ribbon, although other kink-resisting members may be employed in its stead. In this catheter assembly, it is desirable that no kink-resisting member be used in the more proximal sections of the catheter assembly. Also important to the inventive concept of this catheter assembly is the use of a long junction region proximal of the most distal section. The junctions used in this inventive device are typically long conical surfaces between the various tubular members. Normally, a lubricious catheter tubular member is central in the assembly and forms a single lumen from one end of the device to the other.

Figure 1:
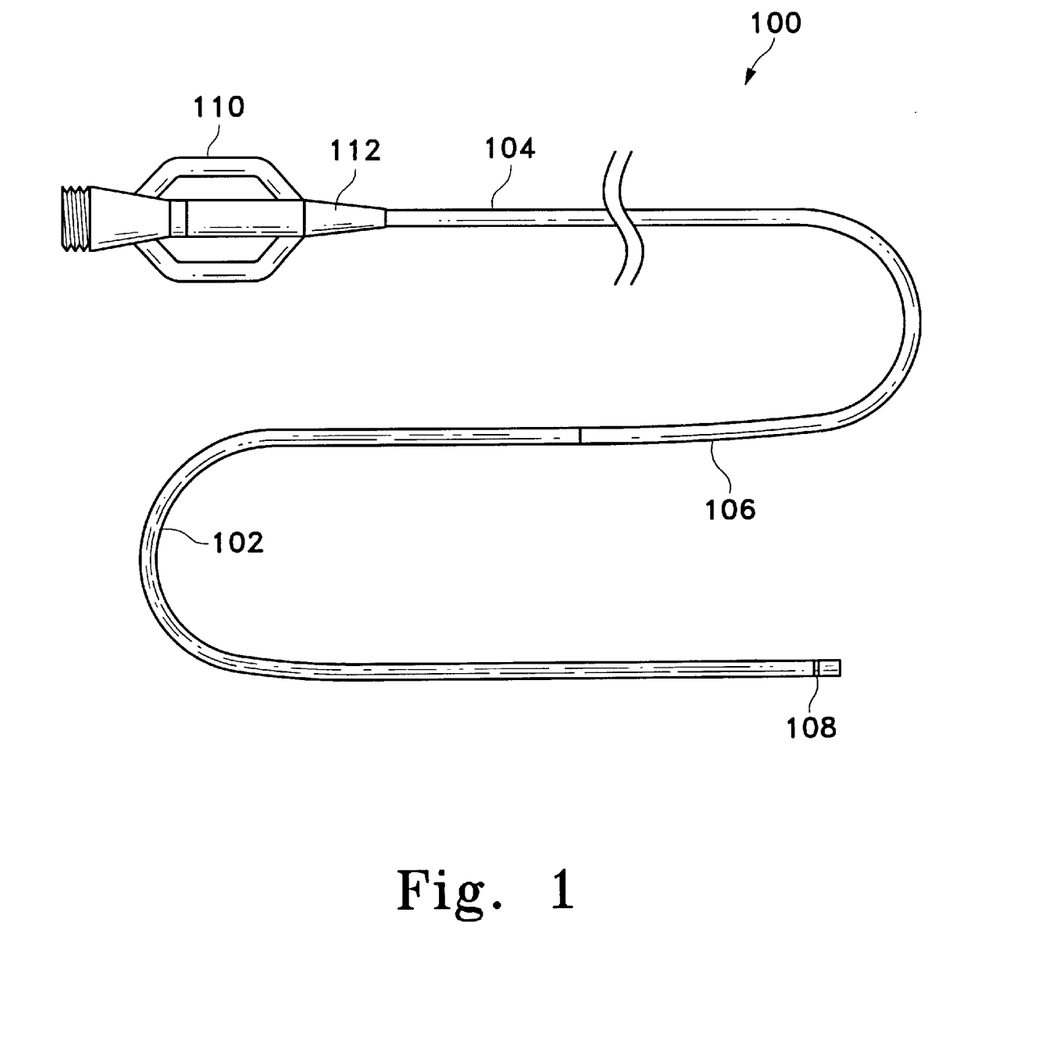
FIG. 1 shows, in a side view, a typical catheter assembly made using the concepts of this invention.

FIG. 1 shows a typical multi-section catheter (100) incorporating the concepts of this invention. This device is particularly suitable for peripheral vascular applications, although, because of its construction, may be used in other services such as neurovascular access. Clearly, it is also suitable for less demanding service such as might be encountered in access and treatment of the heart. One difficulty which has arisen as demands for greater introduction into the target organs has been encountered is that the diameter of the distal section necessarily becomes smaller and smaller. As noted above, it is desirable that to achieve this smaller diameter, that the wall of the catheter become concomitantly thinner. Without additional thought to the design, such a thinner wall may kink or ripple when pushed along a guidewire when mechanical vaso-occlusive devices are pushed through the catheter's lumen. This wall thinning may also result in a catheter's sensitivity to placement of high pressure liquids and potential bursting or separation of joints along such catheter.

This catheter overcomes effectively those noted problems. The catheter shown in FIG. 1 includes a most distal section (102) and a more proximal section (104). Separating and joining more proximal section (104) and most distal section (102) is a joint region (106) which contains the conical joints described below in more detail.

By proper selection of materials, the most distal section (102) is the most flexible portion and the more proximal portion (104) is stiffest and most able to effectively transmit torquing and pushing operations during placement of the device. Junction section (106), because of the nature of its design, varies in flexibility between those of its adjacent sections. Junction section (106), although forming only a small percentage of the overall length of catheter assembly (100), is nevertheless quite lengthy when compared to the diameter of that section. Highly preferred is a catheter shaft which includes no butt joints within the assembly from the proximal end of the catheter shaft to the distal end. By "butt joint," we mean the joining of two adjacent tubular components via a surface which surface is within 5° of perpendicular to the axis of the catheter shaft. For the purposes of this disclosure, we also intend the term "kink-resisting member", except where specifically otherwise specified, to include only metallic braid and coil structures.

Also shown in FIG. 1 are accessories which, although optional from the point of view to their necessity to the invention, are from a practical point of view highly desirable. These accessories include a distal radio-opaque marker (108). It is within the scope of this invention that the catheter assembly (100) have more than one radio-opaque marker if the catheter designer so decides. Dual markers may be used, for instance, with placement of vaso-occlusive members such as coils, braids, or liquid embolic materials. Also shown in FIG. 1 is luer assembly (110) for guidewire and fluids access. A strain relief member (112) of, e.g., a soft, rubbery polymer is also shown.

Typical dimensions for a catheter made using the concepts of this invention are as follows. The overall length of the catheter from distal tip to luer fitting may be in the range from 60–200 cm. For peripheral vascular use, a total catheter length of 85–160 cm. is typically appropriate and most preferably is 105–155 cm. The length of the most distal section (102) is typically in the range of 10–30 cm., most preferably 12.5–25 cm. The outside diameter of the catheter typically is between 30 mils and 50 mils. Preferably, the outer diameter falls between 33 mils and 40 mils. Most desirably, for peripheral access catheter, the more proximal portion (104) is 39 mils, ±1 mil and the distal-most section (104) is 35 mils±2 mils. Obviously, this means that there is an optional taper of the outside diameter at the junction region (106).

Similarly, the inside diameter (or lumen) typically falls between 24 and 30 mils, more preferably 25 and 29 mils. For the preferred catheter of this invention, the distal inside diameter is 26 mils±1 mil and the proximal diameter (in more distal section (104)) is 28 mils±1 mil.

Obviously, these dimensions are not particularly critical to this invention and are selected only as a function of the malady treated and its site within the body.

Furthermore, a catheter made using this inventive concept need not be merely of the two sections of decreasing stiffness as shown in FIG. 1. The catheter may be of three or more discrete sections or may contain sections which vary in stiffness along their length.

Figure 2:
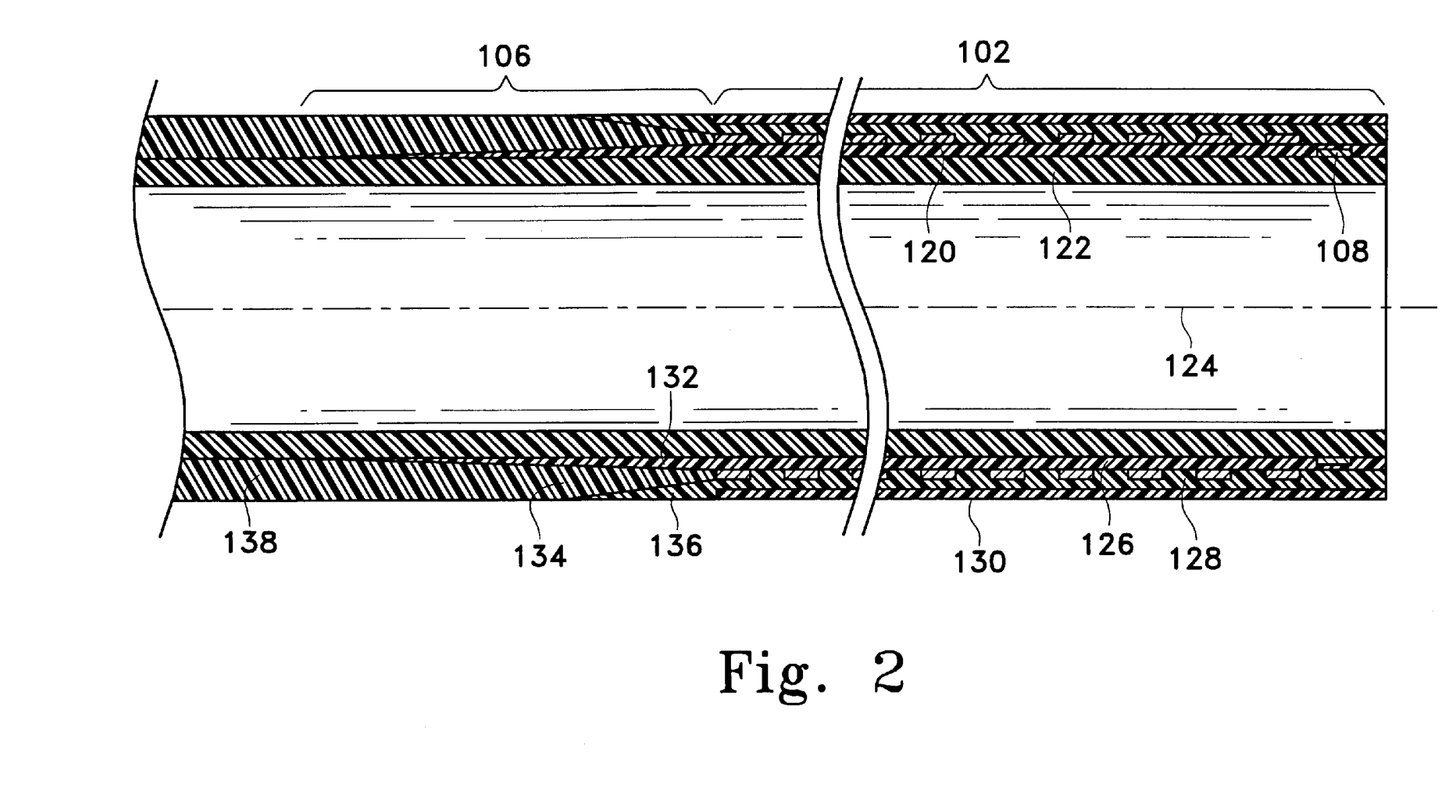
FIG. 2 is a cross-section of the distal-most portion and the junction region of a catheter made according to the invention.

FIG. 2 shows a cross-section of the distal section (102) and the junction region (106) of a catheter made according to this invention.

Figures 4A, 4B:
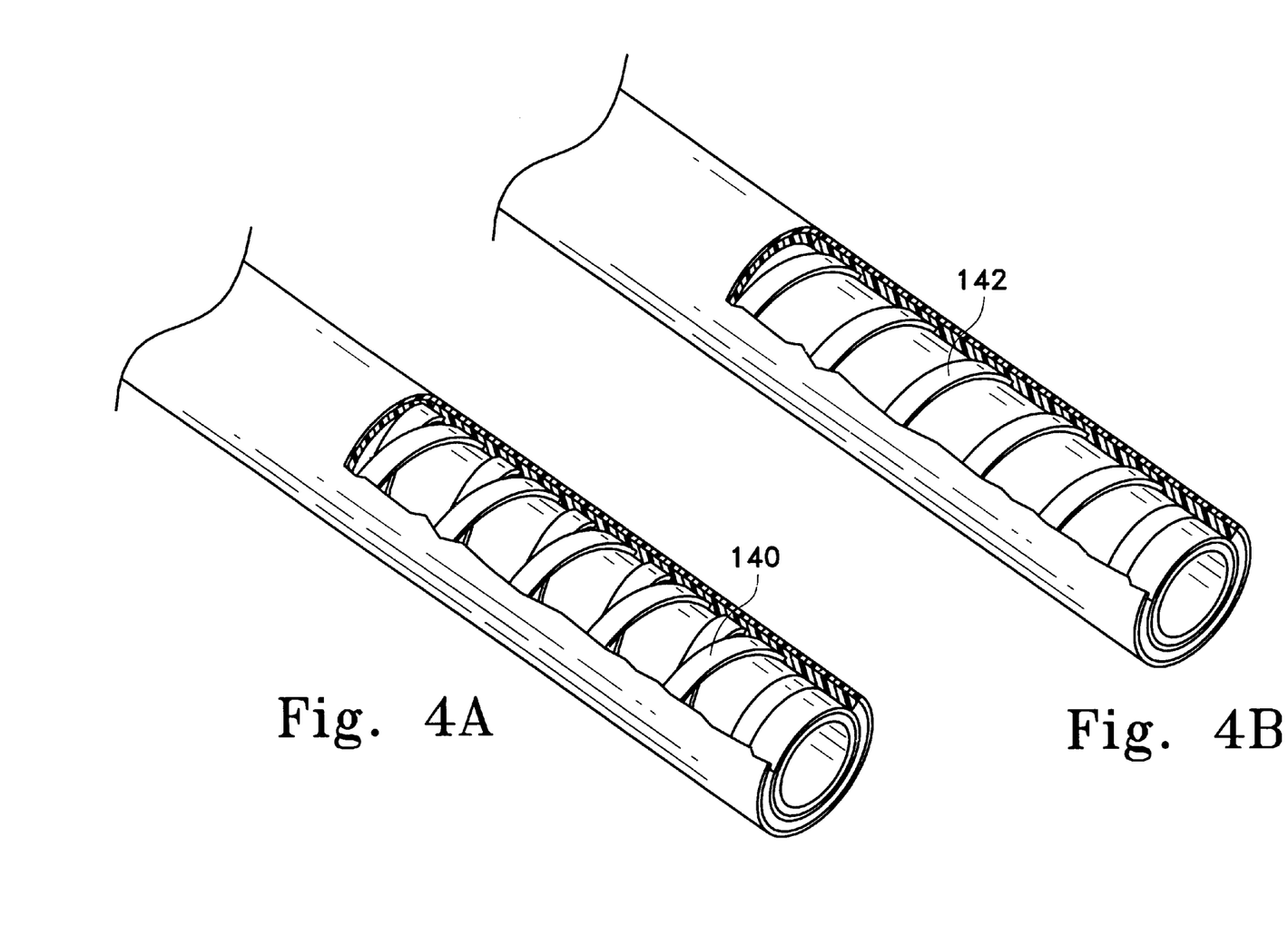
FIG. 4A is a partial cutaway of a distal section of a catheter made according to this invention.
FIG. 4B is a partial cutaway of a distal section of a catheter made according to this invention.

In particular, distal section (102) is made up of a number of polymer layers and a kink-resisting member. Radio-opaque band (108) is also shown in that section (102). The kink-resisting member (120) defines the length of most-distal section (102). The proximal end of kink-resisting member (120) is the proximal most extent of distal-most section (102). Kink-resisting member (120) may be a braid (as shown as (140) in FIG. 4A) or the braid may be unwoven. The kink-resisting member (120) may also be a helically wound coil (142) as is shown in FIG. 4B. It is within the scope of this invention that braid (140) (in FIG. 4A) may be simply a pair of counter-woven helically wound coils such as described as a non-woven braid. It is also within the scope of this invention that kink-resisting member (120) may be made of wires or individual or accumulated and/or woven fibers. By "ribbon" is meant an elongated element having a cross-section which is not square or round, but which cross-section may be rectangular, oval or semi-oval. A ribbon should have an aspect ratio of no more than 0.5:1 (thickness/width). In particular, for the super-elastic alloys described below, particularly those containing nickel and titanium, the thickness and width should be respectively within the range of 0.25 mil to 2.5 mils and a width of 1.0 mil to 10 mils. When metallic wire are similarly often down in the range of 0.20 mil to 2 mils in diameter. Ribbons made from suitable polymers such as liquid crystal polymers (LCP) are of a size similar to those for super-elastic alloys.

As noted above, the material making up the kink-resisting member (120) is preferably a super-elastic alloy such as titanium/nickel materials known as nitinol. These alloys were discovered by the U.S. Naval Ordnance Laboratory. They are described in U.S. Pat. No. 3,174,851 to Buehler et al., U.S. Pat. No. 3,351,463 to Rozner et al., and U.S. Pat. No. 3,753,700 to Harrison et al. Commercial nitinol alloys containing up to about 8% or more of one or more of the members of the Iron Group, e.g., Fe, Cr, Co, etc. of the Periodic Table are considered to be encompassed within the class of super-elastic nickel/titanium alloys suitable for this service.

When using a super-elastic alloy, an additional step may be desirable to preserve the shape of the stiffening braid or coil. For instance, after a braid has been woven using, e.g., 4, 8, 12, or 16 members, some heat treatment may be desirable. Braids which are not treated this way may unravel during subsequent handling or may undertake changes in diameter or spacing during that handling. In any event, the braids are placed on a heat-resistant mandrel, perhaps by weaving them onto that mandrel, and placed in an oven at a temperature of, e.g., 650° to 750° F. for a few minutes. This treatment may anneal the material in the constituent ribbon but in any event provides it with a predictable shape for subsequent assembly steps. After heat-treatment, the braid does retain its shape and most importantly the alloy should retain its super-elastic properties.

Although the ribbons making up the stretch-resistant member (120) shown in FIG. 2 are desirable of the super-elastic alloy material, they need not be. Braids may be made of a mixture of materials, e.g., super-elastic alloy and stainless steel components or of LCPs. Preferred because of cost, strength, and ready availability or stainless steels (SS304, SS306, SS308, SS316, SS318, etc.) and tungsten alloys. In certain applications, particularly in smaller diameter devices, more malleable metals and alloys, e.g., gold, platinum, palladium, rhodium, etc. May be used. A platinum alloy with a few percent of tungsten it is sometimes used because of its high radial opacity.

Suitable non-metallic ribbons and filaments include high performance materials such as those made of polyaramids (e.g., KEVLAR), liquid crystal polymers (LCPs), and carbon fibers.

As noted above, the preferred stretch-resistant member (120) used in this invention is a "woven" braid. By "woven braid" is meant to include tubular constructions in which the ribbons, wires, or filaments making up the construction are woven radially in an in and out fashion as they cross each to form a tubular member having a single lumen. The braid shown in FIG. 4B has a nominal pitch angle of 45°. Clearly the invention is not so limited. Other braid angles from less than 10° to 60° are also suitable. An important variation of this invention is the ability to vary the pitch angle of the kink resisting member, e.g., braid, either at the time it is woven or at the time it is included in the catheter section. Typically, the inner most layer (122) has a smooth inner surface defining the lumen of the catheter. The lumen and catheter axis (124) extend from the distal end of distal section (102) to the proximal end of the catheter as was shown in FIG. 1. Preferred polymeric materials for inner liner (122) are the bridges polymers such as fluorocarbon polymers. Such lubricious polymers include polytetrafluoroethylene (PTFE or TFE), ethylene-chlorofluoroethylene (ECTFE), fluorinated ethylene propylene (FEP), polychlorotrifluoroethylene (PCTFE), polyvinylfluoride (PVF) or polyvinylidenefluoride (PVDF) especially preferred is PTFE. Other materials such as polyethylene, polypropylene, polyvinylchloride (PVC), ethyl vial acetate (EVA), polyurethanes, polyamides, polyethyleneterephthalate (PET), polyamides (nylon) their mixtures and co-polymers are also acceptable.

We have found that when a fluorinated polymer is used as a inner tubing member (122), it is sometimes useful to etch the outside surface of the member to provide a good mechanical surface to which adjacent polymers will readily adhere. Certain procedures using, for instance, treatment with a mixture of aliphatic hydrocarbons and sodium metal as the etching solution is known to be effective in such service.

Although kink-resisting member (120) may be placed directly adjacent inner layer (122), it is desired that kink-resisting member (120) be radially encased by one or more layers, e.g., an inner filler layer (126) and an outer filler layer (128). In this way, slip or shift of the kink-resisting (120) against the typically lubricious inner layer (122) may be avoided. This pair of filler layers (126, 128) adheres to the kink-resisting member (120) and forms a determinate layer which enhances the kink-resisting capabilities of the distal most section (102). Finally, both to soften the outer surface of the most distal section (102) and to lower its stiffness, a distal outer shaft layer (130) is placed on the outside surface of the tubular members discussed above. It is typical that the distal outer shaft layer (130) extend for the entire length of the distal most section (102). Outer filler layer (128) and inner filler layer (126) are typically, but need not be, extensions of tapered components of the assembly joint found in the junction region (106).

We have found that distal most sections made in this way can undergo bends of 1/32th of an inch diameter without visible kinking.

It is desirable that both inner filler layer (126) and outer filler layer (128) be similar, and probably the same material, desirably having a Shore hardness of 45 D–60 D. Preferable it is a Shore 55 D material. The distal outer shaft layer (130) is another material of a Shore hardness 70 A–85 A, preferably about 75 A. Each inner filler layer (126), outer filler layer (128), and distal outer shaft layer (130) may be a variety of materials. Again, the desirably are polymeric and selected materials which tend to tack to each other upon heating. They may also be melt-miscible. In some instances, they may contain ancillary components which act in the manner of adhesives, but such is not necessary. They may be made of heat-shrinkable materials (e.g., irradiated low-density polyethylene) or may be otherwise placed onto the structure. Polyurethanes and their alloys, mixtures, and co-polymers are in this latter class. Preferred polymeric materials for these sections include polyethylene, polypropylene, polyvinylchloride (PVC), ethylvinylacetate (EVA), polyurethanes, polyamides, polyethyleneterephthalate (PET), and their mixtures and co-polymers. Especially preferred materials are mixtures of polyurethanes and polycarbonates sold as Carbothane.

Typically, just proximally of the most distal section (102), may be found the junction region (106). Junction region (106) is, for the purposes of this disclosure, that region proximal of most-distal section (102), which contains any tubing joint which has a tapering surface. Shown in FIG. 2 is a variation in which several tapering surfaces are laminated together to form a long junction region. Many of the benefits of this invention are accomplished when the length of the junction region compared to its diameter are in the range of 12:1 to 3:1 preferably 5:1 to 2.5:1.

In any event, junction region (106) is shown to have extension of inner lubricious layer (122) passing therethrough. A first conical layer (132) having a proximal male conical surface is shown adjacent the lubricious layer (122). It is optionally an extension of inner filler layer (126). Also shown in FIG. 2 is second conical layer (134) having a distal female conical surface which interfits with the male surface on first conical layer (132). Second conical layer (134) may also have a distal male surface which interfits with a proximal female conical surface on third conical layer (136). Third conical layer (136) is preferably a proximal extension of outer filler layer (128). Second conical layer (134) is preferably a distal extension of outer more proximal layer (138). The material making up outer catheter layer (138) may be similar to those found in various polymeric layers found in the distal section (126, 128, 130) but preferably is somewhat stiffer and is of a material which has a Shore hardness of 65–85 D, preferably 70–75 D.

Figure 3:
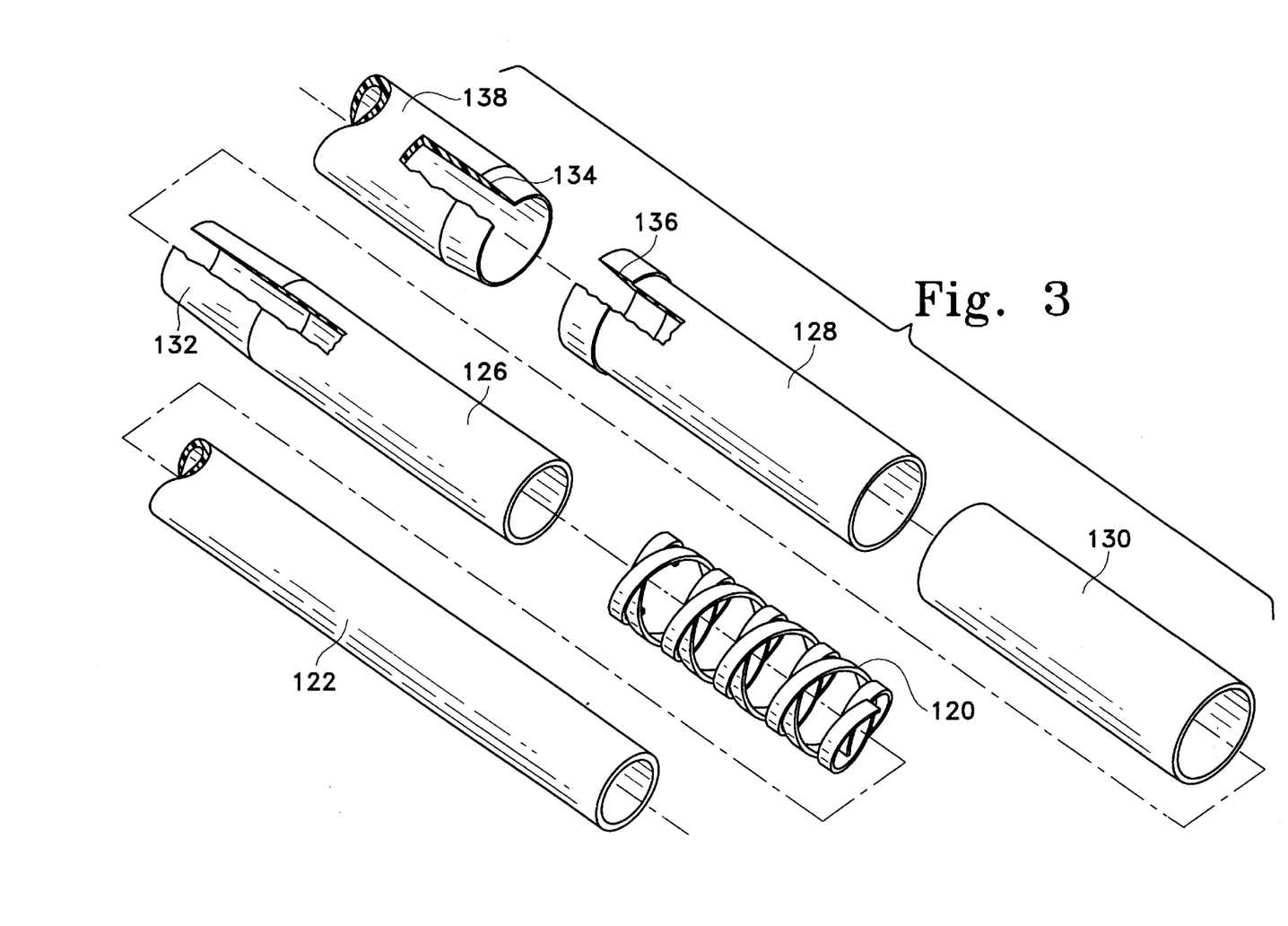
FIG. 3 is an exploded drawing showing various tubular components making up the more distal section of the invention.

FIG. 3 shows an exploded drawing of the components making up both most distal section (102) and junction region (106). The manner of assembling these components will be discussed in more detail below. FIG. 3 show inner lubricious layer (122). Outside of lubricious layer (122) will be found inner filler layer (126) as shown in partial cutaway is the long tapering portion having the outside conical surface (132) which was denominated above the "first conical layer". The kink-resisting member (120) is placed on the exterior surface of inner filler layer (126). Outer filler layer (128) is shown with (by partial cut away) third conical layer (136) having an internal female conical surface. Outer filler layer (128) with its potentially proximally extending third conical layer (136) is situated typically exterior to kink-resisting member (120). Distal outer shaft layer (130) is placed still further exterior to outer filler layer (128) and is approximately the same length as kink-resisting layer (120). Finally, outer catheter layer (138) with its distally extending second conical layer (134) is shown with both a distal male conical surface and an inner female conical surface. As seen in FIG. 3, in the case where the outer (128) and inner (126) filler layers are extension of the tapered components of the assembly joint, the filler layers will be the distal ends of the conical members.

It is within the scope of this invention to include multiple polymeric layers in each of the junction region (106) and the distal most portion (102). It is also within the scope of this invention to coat any of the exterior or interior surfaces of the catheter assembly (100) (FIG. 1) with a lubricious layer which is either chemically bonded to the surface or is merely physically coated to the relevant surface. Description of suitable procedures for producing bonded lubricious coatings is found in U.S. patent applicant Ser. No. 08/060,401 ("Lubricious Catheters"), filed May 12, 1993; Ser. No. 08/235,840 ("Methods for Producing Lubricious Catheters"), filed Apr. 29, 1995; and Ser. No. 08/272,209 ("Lubricious Flow Directed Catheter"), filed Jul. 8, 1994, the entirety of which are incorporated by reference.

Each of the polymers noted herein, with a possible exception of that found in the inner lubricious layer (122) may actually be filled with radio opaque materials such as barium sulfate, bismuth trioxide, bismuth carbonate, powdered tungsten, powdered tantalum or the like so that location of the various portions of the catheter may be radiographically visualized in the human body.

As further within the scope of this invention that the pitch of kink-resisting member (120) vary within most distal section (102). It is desirable in some instances that the pitch of kink-resisting (120) be greater towards the distal end of the more distal section (102) so to provide enhanced flexibility in that region.

The various distal end section (102) and joint region (106) components shown in FIG. 3 which have tapering surfaces are generally made by placing in appropriate sized-tubing section on a mandrel having a desired shape. The section is then stretched until the shapes shown in FIG. 3 are approximated. The component is then removed from its mandrel and cut to appropriate size.

Once appropriately shaped subcomponents as shown in FIG. 3 are made, assembly may begin. First of all, inner lubricious layer (122) is placed on a mandrel and axially stretched so to provide it with axial molecular orientation. It should be noted that the mandrel chosen is one which will provide the change in desired inner diameter discussed above. The various noted elements are assembled as shown. A heat shrinkable tubing is placed on the exterior of this assembly and shrunk down to maintain the various elements in position and hold them there as they are further heated to cause the various polymers to flow into each other and form the conical surfaces as shown, e.g., in FIG. 2. It is to be understood that the conical surface may not have the straight line interfaces as shown in FIG. 2. It is within the scope of the invention that they have some significant amount of curvature within the junction region such as considered to be normal within the scope of this invention.

EXAMPLE

We built several catheter assemblies according to this invention. The distal sections of each catheter were made to have the structure shown in the FIG. 2. The proximal shaft outer covering was 72 D Carbothane, the inner filler layer and outer filler layer with their proximally extending portions in the junction region were 55 D Carbothane, the distal outer shaft layer was 75 A Carbothane. The marker band placed distally at the distal section was a platinum-iridium marker band to minimize thickness. The kink resistant member was a woven braid having eight ribbon members. The ribbons were nitinol and were 0.75 mils thick and 4 mils wide. Each catheter had a proximal section outside diameter of 0.0375 inches (±0.001 inches) a proximal inside diameter of 0.028 inches (±0.001 inches), a distal outside diameter of 0.0350 inches (+0.001 and −0.0015 inches) and a distal inside diameter of 0.026 (±0.001 inches). The mid-junction outside diameter was 0.0375 inches (+0.001 inches and −0.002 inches). We built catheter assemblies having lengths of 105 cm, 135 cm, and 150 cm. For each length, we produced catheters having respectively 14.5 cm and 22.5 cm distal section braid lengths. We coated the more distal portions of each of these catheters with a hydrophilic polymer.

Of these catheters, the 105 centimeter catheters had a dead space volume of 0.50 cc. The 135 centimeter catheters had dead space volumes of 0.62 cc and the 150 centimeter catheters had dead space volumes of 0.68 cc. The tip flexibility for each of the catheters was approximately 0.051 pounds per degree of flexion. The flow rates for the 135 cm catheter was 3.01 cc per second of water, 2.16 cc per second (60% Hypaque-a commercial vascular), and 1.06 cc per second (76% Hypaque). Each of the distal sections of the catheter had a kink-less bend radius of less than $\frac{1}{16}$ of an inch.

This invention has been described and specific examples of provided for clarity. The use of those specifics is not intended to limit the invention in any way. Additionally, to the extent that there are variations of the invention which are within the spirit of the disclosure and yet are equivalent to the inventions found in the claims, it is our intent that those claims cover the equivalent variations as well.

We claim as our invention:

1. An assembled catheter assembly comprising:
   an elongate member having a distal end, a proximal end, a lumen between said proximal end and said distal end, a distal region adjacent said distal end, a proximal region located proximally from said distal region, a polymeric outer filler layer extending along at least a portion of said elongate member, and an axis between said distal end and said proximal end,
   wherein said distal region comprises:
   a.) an inner lubricious layer forming a portion of said lumen,
   b.) a kink-resisting member exterior to said inner lubricious layer having a distal end and a proximal end wherein said proximal region does not contain said kink-resisting member, said polymeric outer layer being exterior to said kink-resisting member,
   c.) a junction region being exterior to said inner lubricious layer and proximal of said kink-resisting member, said junction region being axially adjacent to said proximal end of said kink-resisting member, and wherein said junction region comprises and is assembled from at least two interfitting conical members during at least one assembly step, one conical member having a male conical surface and one conical member having a female conical surface, said one conical member having a male conical surface being slideable with respect to said one conical member having a female conical surface during said at least one assembly step.

2. The catheter assembly of claim 1 where the kink-resisting member is a woven braid member.

3. The catheter assembly of claim 2 where the woven braid member is woven from ribbons or filaments comprising materials selected from the group consisting of polymers, metal alloys, and carbon.

4. The catheter assembly of claim 3 where the metal alloy is a super-elastic alloy.

5. The catheter assembly of claim 3 where the metal alloy is a nickel titanium alloy.

6. The catheter assembly of claim 3 where the woven braid member is woven from LCP filaments.

7. The catheter assembly of claim 1 where the kink-resisting member is a helically wound coil.

8. The catheter assembly of claim 7 where the helically wound coil is wound from ribbons or filaments comprising materials selected from the group consisting of polymers, metal alloys, and carbon.

9. The catheter assembly of claim 1 wherein the ratio of said junction region length to said junction region outer diameter is between 5:1 and 10:1.

10. The catheter assembly of claim 1 where said second conical member has a further outer male conical surface.

11. The catheter assembly of claim 10 further comprising a third conical member having a female conical surface intermitting with said second conical member outer male conical surface.

12. The catheter assembly of claim 10 wherein said polymeric outer filler layer is in contact with said kink-resisting member and extends substantially from the proximal end of said kink-resisting member to the distal end of said elongate member.

13. The catheter assembly of claim 12 further comprising a polymeric inner filler layer interior to and in contact with said kink-resisting member and extending substantially from the proximal end of said kink-resisting member into the distal end of said elongate member.

14. The catheter assembly of claim 13 further comprising a distal outer shaft layer exterior to and in contact with said outer filler layer.

15. The catheter assembly of claim 13 wherein said inner filler layer is a distal end of said first conical member.

16. The catheter assembly of claim 13 wherein the outer filler layer is a distal end of said third conical member.

17. An assembled catheter assembly comprising:
   an elongate member having a distal end, a proximal end, a lumen between said proximal end and said distal end, a distal region adjacent to said distal end, a proximal region located proximally from and contiguously adjacent said distal region, a polymeric outer filler layer extending along at least a portion of said elongate member, and an axis between said distal end and said proximal end, said catheter assembly having no butt joints between said distal end and said proximal end,
   wherein said distal region comprises:
      a.) an inner lubricious layer forming a first portion of said lumen,
      b.) a woven braid member exterior to said inner lubricious layer and having a distal end and a proximal end, said polymeric outer filler layer being exterior to said kink-resisting member,
      c.) a junction region being exterior to said inner lubricious layer and proximal of said woven braid member, said junction region being axially adjacent to said proximal end of said woven braid member,
      and wherein said junction region comprises and is assembled from at least two interfitting conical members during at least one assembly step, one conical member having a male conical surface and one conical member having a female conical surface, said one conical member having a male conical surface being slideable with respect to said one conical member having a female conical surface during said at least one assembly step,
   said junction region having a ration of ajunction region length to a junction region outer diameter of between 3:1 and 12:1,
   and wherein said more proximal region comprises:
      a.) an exterior layer extending from said junction region to said elongate member proximal end,
      b.) said inner lubricious layer extending to said elongate member proximal end, forming the remainder of said lumen and
      c.) a connector opening into said lumen.

18. The catheter assembly of claim 17 wherein the ratio of said junction region length to said junction region outer diameter is between 5:1 and 10:1.

19. The catheter assembly of claim 17 where the woven braid member is woven from ribbons or filaments comprising material selected from the group consisting of polymers, metal alloys, and carbon.

20. The catheter assembly of claim 19 wherein the woven braid member is woven from the metal alloys consisting of super-elastic alloy ribbons.

21. The catheter assembly of claim 20 where the super-elastic alloy is a nickel titanium alloy.

22. The catheter assembly of claim 19 where the woven braid member is woven from LCP filaments.

23. The catheter assembly of claim 17 where said second conical member has a further outer male conical surface.

24. The catheter assembly of claim 23 further comprising a third conical member having a female conical surface interfitting with said outer male conical surface of said second conical member.

25. The catheter assembly of claim 23 wherein said polymeric outer filler layer is in contact with said woven braid member and extends substantially from the proximal end of said woven braid member to the distal end of said elongate member.

26. The catheter assembly of claim 25 further comprising a polymeric inner filler layer interior to and in contact with said woven braid member and extending substantially from the proximal end of said woven braid member into the distal end of said elongate member.

27. The catheter assembly of claim 26 further comprising a distal outer shaft layer exterior to and in contact with said outer filler layer.

28. The catheter assembly of claim 26 wherein said inner filler layer is the distal end of said first conical member.

29. The catheter assembly of claim 26 wherein the outer filler layer is a distal end of said third conical member.

* * * * *